United States Patent
Girton

(10) Patent No.: US 6,537,300 B2
(45) Date of Patent: Mar. 25, 2003

(54) IMPLANTABLE OBSTRUCTION DEVICE FOR SEPTAL DEFECTS

(75) Inventor: Timothy Girton, Minneapolis, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/867,951

(22) Filed: May 30, 2001

(65) Prior Publication Data

US 2002/0183786 A1 Dec. 5, 2002

(51) Int. Cl.[7] .............................................. A61B 17/00
(52) U.S. Cl. ...................... 606/213; 606/215
(58) Field of Search .................. 606/213, 78, 157, 606/142, 143, 151, 232, 215, 108; 128/887, 898

(56) References Cited

U.S. PATENT DOCUMENTS

| | | | |
|---|---|---|---|
| 3,874,388 A | * 4/1975 | King et al. ............. 128/334 R |
| 5,108,420 A | 4/1992 | Mark ......................... 606/213 |
| 5,383,928 A | 1/1995 | Scotts et al. .................. 623/1 |
| 5,695,499 A | * 12/1997 | Helgerson et al. .......... 606/108 |
| 5,853,422 A | * 12/1998 | Huebsch et al. ............. 606/213 |
| 5,855,599 A | 1/1999 | Wan ............................... 623/1 |
| 5,925,060 A | * 7/1999 | Forber ........................ 606/191 |
| 5,944,738 A | 8/1999 | Amplatz et al. ............. 606/213 |
| 5,976,147 A | 11/1999 | Ruiz ........................... 606/213 |
| 6,077,291 A | 6/2000 | Das ............................. 606/213 |
| 6,080,182 A | 6/2000 | Shaw et al. .................. 606/213 |
| 6,129,672 A | * 10/2000 | Seward et al. .............. 600/463 |
| 5,634,936 A1 | 5/2001 | Linden et al. ............... 606/213 |
| 6,283,983 B1 | * 9/2001 | Makower et al. ........... 606/198 |
| 6,306,177 B1 | * 10/2001 | Felt et al. .................. 623/23.6 |
| 6,312,402 B1 | * 11/2001 | Hansmann ................... 604/22 |

FOREIGN PATENT DOCUMENTS

| | | |
|---|---|---|
| EP | 0 920 842 | 6/1999 |
| EP | 1 046 375 A1 | 10/2000 |
| WO | WO 99/47075 | 9/1999 |
| WO | WO 00/12012 | 3/2000 |
| WO | WO 01/30266 A1 | 5/2001 |

* cited by examiner

Primary Examiner—John J. Calvert
Assistant Examiner—Alissa L. Hoey
(74) Attorney, Agent, or Firm—Westman, Champlin & Kelly, P.A.

(57) ABSTRACT

An implantable medical device for at least partially obstructing a septal defect is disclosed. The implantable medical device includes an obstruction mechanism connected to a non-linear elongated tissue-puncturing end.

14 Claims, 4 Drawing Sheets

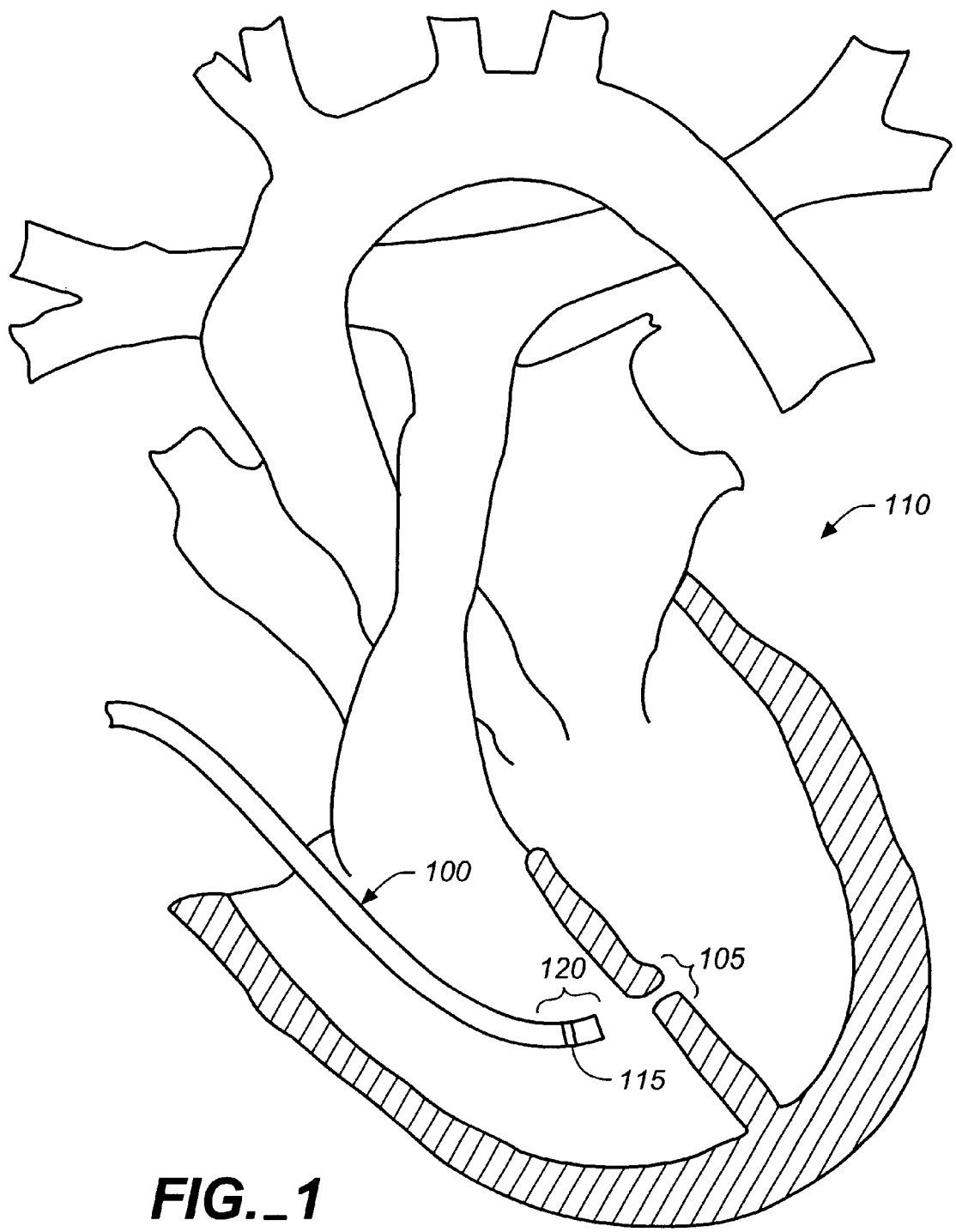
FIG._1

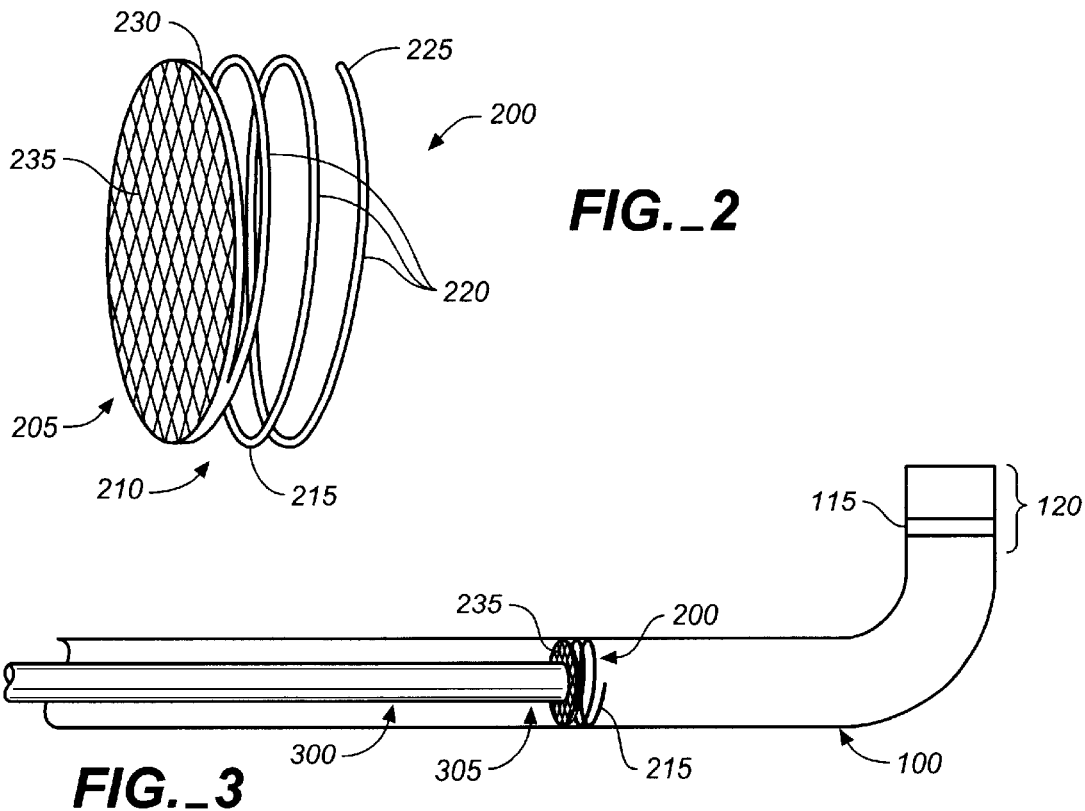
FIG._2
FIG._3
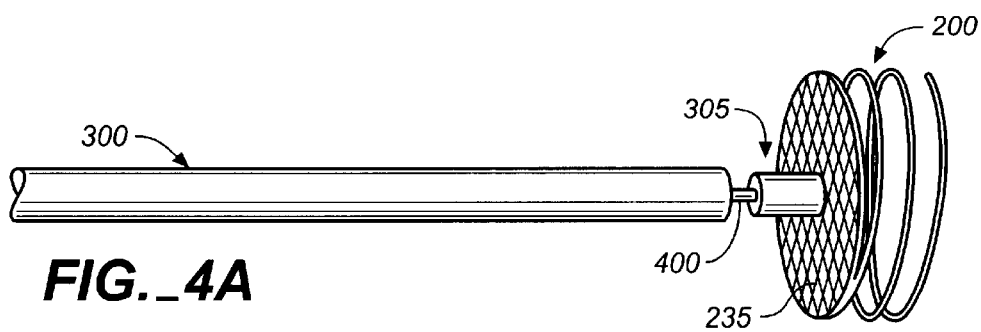
FIG._4A
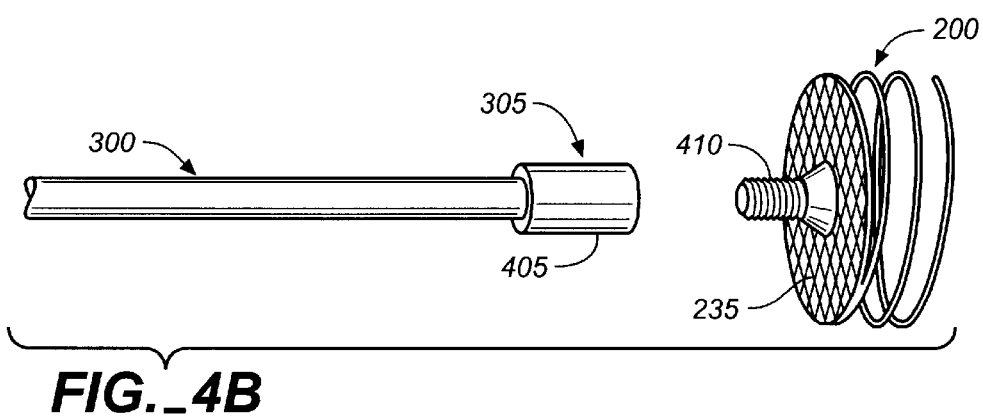
FIG._4B

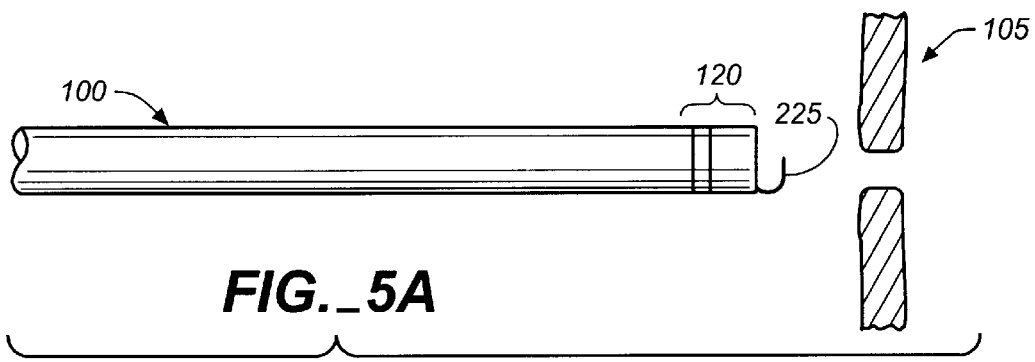
FIG._5A
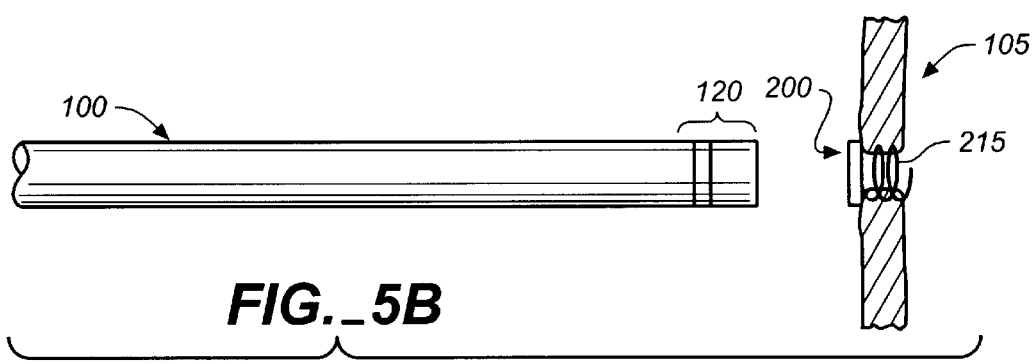
FIG._5B
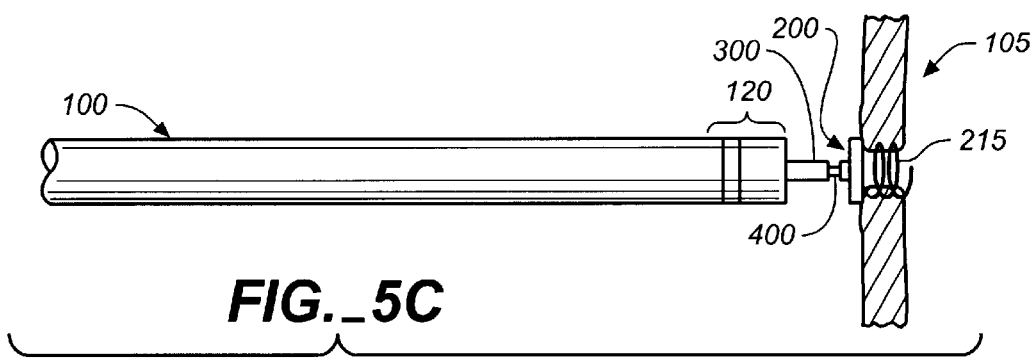
FIG._5C
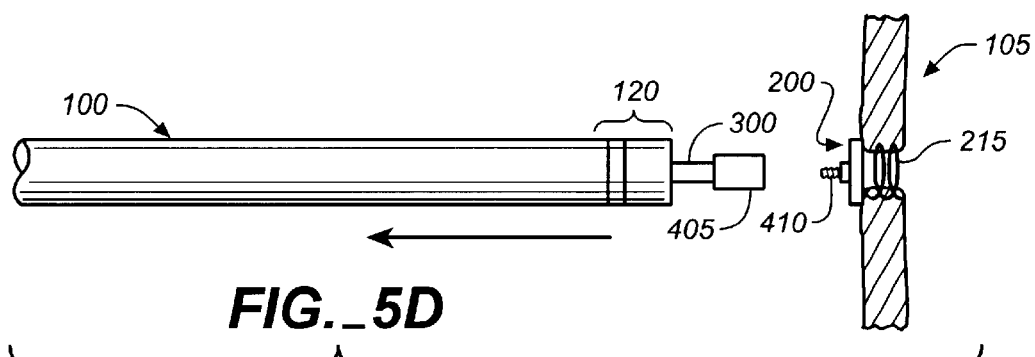
FIG._5D

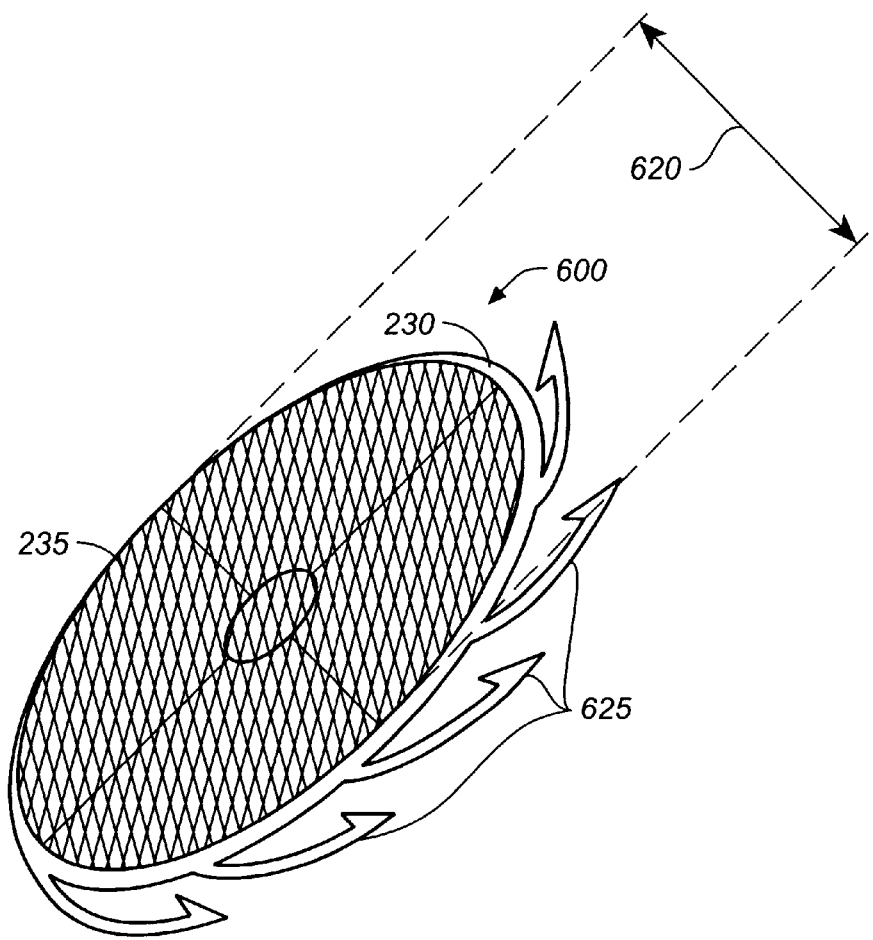
FIG._6A
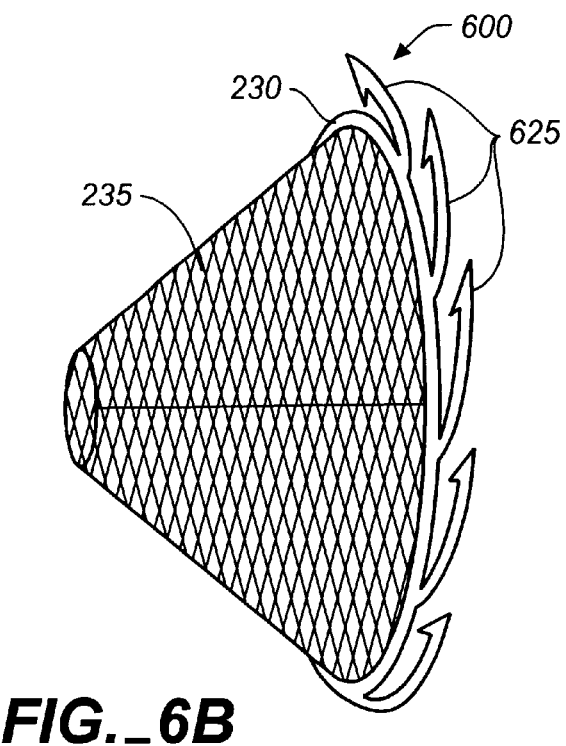
FIG._6B

IMPLANTABLE OBSTRUCTION DEVICE FOR SEPTAL DEFECTS

BACKGROUND OF THE INVENTION

The present invention deals with an implantable medical device. While the device could be utilized in the context of a variety of body spaces, and particularly in the context of a variety of septal defects, the present description, for the sake of brevity, will be focused primarily on the treatment of ventricular septal defects. Accordingly, the present invention deals with an implantable medical device for at least partially obstructing a ventricular septal defect.

A ventricular septal defect is characterized by incomplete closure (i.e., a hole) in the intraventricular septum, the heart muscle forming a wall between ventricles within the heart. The intraventricular septum is meant to prevent blood passing from one ventricle to the next. A septal defect can undesirably allow blood to flow from one ventricle to the other, forcing some heart chambers to pump extra blood. This increase in blood can potentially cause the heart to dilate, a weakening of the heart muscle, and pressures in the pulmonary arteries to increase (pulmonary hypertension). In addition, when the intraventricular septum is broken, an undesirable mixing of oxygen-depleted blood from the veins with oxygenated blood going to the arteries is a potential problem. In many instances, these consequences can be minimized or even avoided through a natural or treatment-based obstruction of the septal defect.

The size of ventricular septal defects is variable. Small-to-medium sized defects often close naturally and spontaneously. Many of the larger defects, however, require surgical treatment. If a substantial sized defect is not properly treated, then pressures in the pulmonary arteries may become very high and induce undesirable changes in the arteries themselves. Eventually, if the defect is not corrected, then conditions can deteriorate until even a successful closure of the defect will no longer improve the patient outcome.

Different implantable medical devices have been developed for obstructing ventricular septal defects. Intravascular devices, such as catheters and guide wires, have been used to deliver a variety of these devices to a specific location, such as within a particular ventricle, within a patient's heart. A variety of simple and complex devices are known to be deliverable to a septal defect through a catheter.

One class of catheter-delivered devices designed for the treatment of septal defects are self-expanding defect obstructing devices. A rod-like element is typically connected to these devices and utilized to push the devices from the end of a delivery catheter into a location proximate a septal defect, thereby causing an expansion of the device as it leaves the catheter. The expanded devices are typically maneuvered relative the defect until a secured position, a position where the device will stay in place and cause an obstruction of blood flow through the defect, is located. When the expanding devices have been maneuvered to a secured position, they are typically detached from any catheter, guide wire, or rod-like element utilized for intravascular placement. The expanding devices are left in a location proximate the septal defect and are intended to obstruct blood flow through the defect.

Some implantable self-expanding defect obstructing devices include separate extending portions that expand on both sides of a septal defect and into both of the heart chambers that are connected by the defect. Other devices are balloon-actuated devices, wherein expansion occurs as a result of inflation of extending members. Still other devices include mechanically expanding extending members that collapse (i.e., during delivery through a catheter) and can be extended (i.e., in a location proximate a septal defect) utilizing a mechanically maneuverable frame. Other devices are constructed of shape-memory based material, allowing the device to be manipulated into a collapsed shape and inserted into a catheter. Upon being pushed out of the catheter, these devices regain their original shape (i.e., a shape convenient for obstructing a septal defect).

Designing an effective implantable medical device for the obstruction of a septal defect presents special challenges. Many self-expanding devices suffer from deployment problems (i.e., incomplete opening of extending members or an error in the functionality of the extending member deployment mechanics). Many lack the ability to be precisely and effectively positioned relative a septal defect. In many instances, the shape of known implantable devices fails to effectively accommodate the often complex shape of a septal defect. With most known devices, recovery of a deployed device is difficult if not impossible. Many known devices require highly complex manufacture processes.

SUMMARY OF THE INVENTION

One aspect of the present invention pertains to an implantable medical device for at least partially obstructing a septal defect. The implantable medical device includes an obstruction mechanism connected to a non-linear elongated tissue-puncturing end.

Another aspect of the present invention pertains to an implantable device, deliverable via a vascular catheter, of a size and overall flexibility to lodge in an area of tissue located proximate a septal defect, and suitable for at least partially obstructing the septal defect. The implantable device includes an elongated delivery member having a distal end. An obstruction mechanism is connected to a coil that includes a puncturing end. The obstruction mechanism includes a ring-shaped structure having an interior portion. A material covering substantially fills the interior portion of the ring-shaped structure. A connection between the distal end of the elongated delivery member and the obstruction mechanism enables the obstruction mechanism to be rotated.

Yet another aspect of the present invention pertains to a method for at least partially obstructing a septal defect in a heart by implanting a medical device. The method first includes the step of placing a distal end of a catheter in a location proximate the septal defect. Next, an elongated delivery member is utilized to push an obstruction device through the catheter until a puncturing member portion of the obstruction device extends from the distal end of the catheter. Then, with the puncturing member, an area of tissue proximate the septal defect is punctured. Next, the obstruction device is rotated such that a non-linear tissue engaging section of the obstruction device, which is connected to the puncturing member, becomes substantially embedded in the area of tissue proximate the septal defect. Finally, the catheter and elongated delivery member are removed from the heart.

BRIEF DESCRIPTION OF THE DRAWINGS

FIG. 1 is a partial sectioned view of a heart, wherein a catheter is shown extending toward a ventricular septal defect.

FIG. 2 is a perspective side view of an implantable medical device.

FIG. 3 is a partial sectioned view of the implantable medical device inserted within the catheter.

FIG. 4A is a side view of an embodiment of the implantable medical device, wherein the implantable medical device is attached to an elongated delivery member that includes an electrolytic joint.

FIG. 4B is a side view of an embodiment of the implantable medical device and an elongated delivery member, wherein the delivery member includes a first threaded member and the medical device includes a second threaded member that functionally corresponds to the first threaded member.

FIGS. 5A to 5D are partial sectioned views of the ventricular septal defect, shown relative the catheter, and illustrate various procedural elements associated with using the implantable medical device.

FIG. 6A is a perspective side view of another embodiment of an implantable medical device.

FIG. 6B is a side view of the implantable medical device of FIG. 6A in a collapsed delivery position.

DETAILED DESCRIPTION OF ILLUSTRATIVE EMBODIMENTS

FIG. 1 illustrates a partial sectioned view of a heart, wherein a catheter 100 extends toward a ventricular septal defect 105. Catheter 100 is shown having a radio-opaque band 115 at a distal end 120. As is known in the art, radio-opaque band 115 assists in the guidance of catheter 100 through a vascular system and through heart 110 utilizing principles of radiography or fluoroscopy. As is illustrated, distal end 120 of catheter 100 has been guided so as to extend to a position proximate ventricular septal defect 105.

While, for the sake of brevity, the present invention will be described in the context of ventricular septal defects, the scope of the present invention should not be limited to that context. For instance, the present invention could just as easily be applied in the context of atrial septal defects. In addition the present invention could be applied in the context of a variety of other body spaces.

FIG. 2 illustrates a perspective side view of an implantable medical device 200 in accordance with an embodiment of the present invention. Device 200 includes an obstruction mechanism 205 connected to a non-linear elongated tissue-puncturing end 210.

Non-linear elongated tissue-puncturing end 210 comprises a coil 215 that includes a tissue engaging section 220 and a puncturing member 225. Tissue engaging section 220 illustratively interconnects obstruction mechanism 205 and puncturing member 225.

In accordance with the FIG. 2 embodiment of the present invention, obstruction mechanism 205 includes a material supporting member 230 attached to a material covering 235. Material supporting member 230 is illustratively a ring-shaped structure having an interior portion (portion inside of the ring) that is substantially filled by material covering 235. In accordance with one embodiment, material covering 235 is, by design, configured to physically obstruct blood flow through septal defect 105 (FIG. 1), when device 200 has been implanted relative to the defect. In accordance with one embodiment, material covering 235 is a sheet of polytetrafluroethylene (PTFE) or other biocompatible material (degradable or not).

In accordance with another embodiment of the present invention, material covering 235 can be constructed of a material designed to act as a therapeutic agent. Illustratively, material covering 235 can be constructed of or contain a bioactive material, such as a drug, protein, cells or genetic material, useful for the medical treatment of a ventricular septal defect or other medical disorder.

In accordance with one embodiment, material covering 235 can be constructed of, or have an attached collection of, living cells that promote tissue regeneration within the human body. Illustratively, the cells could be a number of types including but not limited to fibroblast, endothelial cells, smooth muscle cells or stemt cells.

In accordance with other embodiments, material covering 235 can be constructed of or include a different bioactive material selected or designed to encourage cell growth at the site of a septal defect. The material can illustratively be a natural bio-material, such as collagen, gelatin, fibrin, fibronectin, fibriogen, hyaluronic acid, polysaccharides, or proteoglycans, elastin or any combination thereof; or a combination of natural bio-materials and synthetic absorbable materials.

In accordance with still other embodiments, material covering 235 can be constructed of or include a material that encourages cell growth within a targeted portion of a septal defect and then is specifically designed or selected to be biologically absorbed by the human body. While there are many materials that can be utilized as material covering 235, two that are biologically absorbable and encourage cell growth are polylactic acid (PLA) and polyglycolic acid (PGA). In accordance with one embodiment, a mixture or composite composition comprising PLA and PGA could be utilized. Other potential materials that could be incorporated into material covering 235, and that may encourage cell growth, include polymers containing e-caprolactone, trimethylene carbonate, and p-dioxanone. The materials listed above should be considered only examples of the many materials within the scope of the present invention that could be utilized in the construction of material covering 235.

It should be noted that implantable medical devices having configurations other than the precise configuration illustrated by device 200 in FIG. 2 should be considered within the scope of the present invention. For example, non-linear elongated tissue-puncturing end 210 could be formed to include a single-layer coil 215 (or double-layer, quadruple-layer, etc.) tissue engaging section 220 rather than the three-layer coil 215 configuration illustrated in FIG. 2. In addition, material supporting member 230 could be formed in a shape other than the illustrated ring-shaped structure. Finally, material covering 235 need not completely fill an interior portion of a material supporting member 230. For instance, in accordance with one embodiment of the present invention, material covering 235 could be a therapeutic agent disposed circumferentially on material supporting member 230. In accordance with one embodiment, a therapeutic agent could be further disposed on at least one portion of non-linear elongated tissue-puncturing end 210.

Implantable medical device 200 is illustratively of a size and overall flexibility to be deliverable through a tubular delivery device, such as catheter 100 in FIG. 1. FIG. 3 is an illustration of implantable medical device 200 as it is being delivered through catheter 100. The same reference numerals are used in FIG. 3 for elements that are the same or similar to those elements illustrated in FIGS. 1 and 2.

In FIG. 3, an elongated delivery member 300 is being utilized to push medical device 200 through catheter 100 towards catheter distal end 120. As illustrated, device 200 is being delivered with coil 215 in a non-compressed state. In accordance with one embodiment of the present invention, coil 215 is constructed of a material having shape-memory characteristics, such as nitinol. In addition to or in place of nitinol, different super-elastic or pseudo-elastic shape recovery alloys, or shape memory polymers (i.e., urethanes) could be utilized in the construction of coil 215. Other materials having shape-memory characteristics (i.e., certain metals) should be considered within the scope of the present invention.

Utilizing shape-memory material in the construction of coil 215 enables device 200 to be delivered through catheter 100 with coil 215 in a compressed state, wherein frictional forces between catheter 100 and device 200, created while device 200 is being pushed through catheter 100, causes the compression of coil 215. Illustratively, due to an incorporation of material having shape-memory characteristics, as device 200 is pushed from distal end 120 of catheter 100 and constriction forces between catheter 100 and device 200 are eliminated, coil 215 assumes a non-compressed shape.

In accordance with embodiments of the present invention, there are several different ways that a distal end 305 of elongated delivery member 300 could connect to implantable medical device 200. In accordance with the embodiment pictured in FIG. 3, there is no fixed connection between distal end 305 and device 200. Distal end 305 illustratively engages material covering 235 in a non-fixed manner such that delivery member 300 can be disengaged from material covering 235 and device 200 simply by proximally withdrawing delivery member 300.

Turning to FIG. 4A, in accordance with an embodiment of the present invention, an alternate connection between elongated delivery member 300 and medical device 200 is illustrated. The same reference numerals are used in FIG. 4A for elements that are the same or similar to those elements illustrated in previously described embodiments.

FIG. 4A is a side view of medical device 200, which is fixedly attached to elongated delivery member 300. Illustratively, distal end 305 of delivery member 300 includes a portion that is fixedly attached to material covering 235 of medical device 200. Severable joint 400 interconnects distal end 305 with the rest of delivery member 300. Severable joint 400 illustratively includes means for severing medical device 200 from delivery member 300. For example, in accordance with one embodiment, severable joint 400 is an electrolytically severable joint, wherein severable joint 400 is constructed of a material that is more susceptible to dissolution via electrolysis in blood (or other ionic media) than the material used to construct medical device 200 and delivery member 300 (including distal end 305). Accordingly, in response to an electrolytic control signal, severable joint 400 dissolves, thereby disengaging medical device 200 from all or most of delivery member 300. In accordance with one embodiment, severable joint 400 attaches directly to material covering 235 and distal end 205 is connected to joint 400 and located just proximal thereof.

Turning to FIG. 4B, in accordance with an embodiment of the present invention, yet another alternative connection between elongated delivery member 300 and medical device 200 is illustrated. The same reference numerals are used in FIG. 4B for elements that are the same or similar to those elements illustrated in previously described embodiments.

FIG. 4B is a side view of an embodiment of medical device 200 and elongated delivery member 300. Distal end 305 of delivery member 300 includes a first threaded member 405. A second threaded member 410 is fixedly connected to material covering 235 of device 200 and functionally corresponds to the first threaded member. Illustratively, the first and second threaded members 405 and 410 can be desirably engaged and disengaged by rotating delivery member 300 and engaging and disengaging the threaded members 405 and 410. In accordance with one embodiment, when the first and second threaded members are solidly engaged, further rotation of delivery member 300 enables rotation of device 200. For reasons described below in relation to FIGS. 5A–5D, such rotation of device 200 can be desirable during implantation of medical device 200.

FIGS. 5A–5D illustrate a series of partial sectioned views of ventricular septal defect 105, shown relative to catheter 100. The same reference numerals are used in FIGS. 5A–5D for elements that are the same or similar to those illustrated in previously described embodiments.

With reference to FIGS. 5A–5D and to the previously described Figures, procedural elements associated with implanting medical device 200, in accordance with embodiments of the present invention, will now be described.

As is represented by FIG. 1, catheter 100 is initially steered into a location such that distal end 120 is placed proximate septal defect 105. Typically, the positioning of catheter 100 is aided by the use of a steerable guide wire (not illustrated). As was discussed above in relation to FIG. 1, radio-opaque band 115 may be used to assist in the steering of catheter 100.

When catheter 100 has been positioned relative to septal defect 105, any guide wire that has been utilized is typically removed. Next, as was discussed in relation to FIG. 3, utilizing elongated delivery member 300, medical device 200 is then pushed through catheter 100. Medical device 200 is illustratively pushed until puncturing member 225 extends from distal end 120 of catheter 100 (see FIG. 5A).

Next, with puncturing member 225, an area of tissue proximate septal defect 105 is punctured. After the tissue has been punctured, medical device 200 is rotated such that a substantial portion of the coil 215 portion of medical device 200 becomes embedded in the tissue proximate septal defect 105. In accordance with one embodiment, during the rotation step, medical device 200 is physically and gradually transferred out of catheter 100.

In accordance with additional embodiments of the present invention, there are several ways in which device 200 could be rotated during the implantation process. In accordance with one embodiment, medical device 200 is rotated by first ensuring maintenance of a secure engagement between distal end 305 of delivery member 300 and material covering 235, and then rotating delivery member 300. The engagement between distal end 305 and material covering 235 could illustratively be a frictional engagement (FIG. 3), a severable joint engagement (FIG. 4A), a threaded engagement (FIG. 4B), or another similar engagement.

In accordance with another embodiment, medical device 200 is rotated by first ensuring maintenance of a frictional engagement between distal end 120 of catheter 100 and a circumference of device 200. Then, catheter 100 is rotated, thereby rotating device 200. FIG. 5B illustrates device 200 after it has been rotated out of the grip of catheter 100 and into an embedded position within tissue proximate septal defect 105.

In accordance with embodiments wherein medical device 200 is fixedly connected to delivery member 300 through a severable joint 400, FIG. 5C illustrates device 200 after it has been rotated into an embedded position within tissue proximate septal defect 105. Illustratively, the next step is to sever joint 400 in order to eliminate all connections between member 300 and device 200.

In accordance with embodiments wherein medical device 200 is connected to delivery member 300 through a threaded connection between threaded members 405 and 410, FIG. 5D illustrates device 200 after delivery member 300 has been rotated so as to disengage threaded member 405 from 410. Device 200 is left embedded in the tissue proximate defect 105.

Illustratively, a subsequent step in each of the above-described embodiments is to remove catheter 100 and delivery member 300 from heart 110 (FIG. 1). Medical device 200 is left embedded in tissue relative to septal defect 105 such that septal defect 105 at least partially obstructs blood flow from one side of defect 105 to the other.

FIG. 6A is a perspective side view of an implantable medical device 600 in accordance with another embodiment of the present invention. The same reference numerals are used in FIG. 6A for elements that are the same or similar to those elements illustrated in previously described Figures.

Medical device 600 includes a material supporting member 230 attached to a material covering 235. Material supporting member 230 and material covering are configured and operate as described above in relation to other embodiments of the present invention. Device 600 illustratively can be attached to a delivery member (such as delivery member 300) as described above in relation to previous embodiments.

Medical device 600 differs from previous embodiments. In accordance with an embodiment of the present invention, medical device 600 includes a radius 620 that is significantly larger than that of a catheter (such as catheter 100 in FIG. 3) or other delivery mechanism through which device 600 might be delivered. In accordance with one embodiment, radius 620 is up to three times the diameter of an associated delivery device.

Medical device 600 includes an attached plurality of non-linear elongated tissue-engaging mechanisms 625 (an illustrative few have been labeled) disposed around a periphery of material supporting member 230. In accordance with one embodiment, mechanisms 625 are configured to engage tissue proximate a septal defect (such as defect 105 in FIG. 1) in a manner that enables the defect to be at least partially obstructed by device 600. As described above, material covering 235 could illustratively be constructed of a material suitable to supplement device 600 and further encourage obstruction of the defect.

FIG. 6B is a side view of implantable medical device 600 in a collapsed delivery or folded cone shape or position. The same reference numerals are used in FIG. 6B for elements that are the same or similar to those elements illustrated in previously described Figures. In FIG. 6B, device 600 illustratively includes material covering 235, material supporting member 230 and non-linear elongated tissue-engaging mechanisms 625.

In accordance with an embodiment of the present invention, because device 600 includes a diameter 620 that is greater than the diameter of an associated delivery mechanism (such as catheter 100 in FIG. 1), device 600 is illustratively collapsible into a shape suitable for delivery. FIG. 6B is an illustration of medical device 600 in an embodiment of a collapsed position. In accordance with one embodiment, medical device 600 includes material having shape memory characteristics that cause device 600 to transform from the FIG. 6B collapsed configuration to the FIG. 6A non-collapsed configuration, the transformation illustratively occurring as device 600 exits or is pushed out of a delivery device (such as catheter 100 in FIG. 1).

It should be pointed out that while diameter 620 (FIG. 6A) and the collapsed position illustrated in FIG. 6B have been depicted with medical device 600, these features and the associated characteristics could just as easily be applied in the context of previously described embodiments, such as in the context of device 200.

Although the present invention has been described with reference to preferred embodiments, workers skilled in the art will recognize that changes may be made in form and detail without departing from the spirit and scope of the invention.

What is claimed is:

1. An implantable medical device for at least partially obstructing a septal defect, comprising:
    an obstruction mechanism; and
    a non-linear elongated tissue-puncturing end connected to the obstruction mechanism, wherein the non-linear elongated tissue-puncturing end includes a coil having a tissue engaging section and a puncturing member, and wherein the tissue engaging section interconnects the obstruction mechanism and the puncturing member.

2. An implantable device, deliverable via a vascular catheter, of a size and overall flexibility to lodge in an area of tissue located proximate a septal defect, and suitable for at least partially obstructing the septal defect, comprising:
    an elongated delivery member having a distal end;
    an obstruction mechanism comprising a ring-shaped structure having an interior portion and a connection to a coil that includes a puncturing member;
    a material covering that substantially fills the interior portion of the ring-shaped structure; and
    a connection between the distal end of the elongated delivery member and the obstruction mechanism, wherein the connection enables the obstruction mechanism to be rotated.

3. The implantable device of claim 2, wherein the connection comprises an engagement between a first threaded member disposed on the distal end of the elongated delivery member and a functionally corresponding second threaded member disposed on the material covering.

4. The implantable device of claim 2, wherein the connection comprises a frictional engagement between the distal end of the elongated delivery member and the material covering.

5. The implantable device of claim 2, wherein the material covering is constructed of a material that is a therapeutic agent.

6. The implantable device of claim 2, wherein the material covering is constructed of a bioactive material.

7. The implantable device of claim 6, wherein the bioactive material is a biologically absorbable material that encourages cell growth.

8. A method for at least partially obstructing a septal defect in a heart by implanting a medical device, comprising:
    placing a distal end of a catheter in a location proximate the septal defect;
    utilizing an elongated delivery member to push an obstruction device through the catheter until a puncturing member portion of the obstruction device extends from the distal end of the catheter;
    puncturing, with the puncturing member, an area of tissue proximate the septal defect;

rotating the obstruction device such that a non-linear tissue engaging section of the obstruction device, which is connected to the puncturing member, becomes substantially embedded in the area of tissue proximate the septal defect; and removing the catheter and elongated delivery member from the heart.

9. The method of claim 8, wherein rotating the obstruction device comprises:

maintaining a frictional engagement between the catheter and a circumference of the obstruction device; and rotating the catheter.

10. The method of claim 8, wherein rotating the obstruction device comprises:

maintaining an engagement between the elongated delivery member and the obstruction device; and rotating the elongated delivery member.

11. The method of claim 10, wherein maintaining an engagement between the elongated delivery member and the obstruction device comprises:

maintaining a frictional engagement between the elongated delivery member and a material covering portion of the obstruction device.

12. The method of claim 10, wherein maintaining an engagement between the elongated delivery member and the obstruction device comprises:

maintaining a threaded engagement between a first threaded member disposed on the distal end of the elongated delivery member and a second threaded member that functionally corresponds to the first threaded member and is disposed on the obstruction device.

13. The method of claim 12, wherein removing the catheter and elongated delivery member from the heart comprises:

disengaging the first threaded member from the second threaded member;

removing the elongated delivery member from the catheter and from the heart; and removing the catheter from the heart.

14. The method of claim 10, wherein removing the catheter and elongated delivery member the heart comprises:

disengaging the elongated delivery member from the obstruction device by severing a joint therebetween;

removing the elongated delivery member from the catheter and from the heart; and removing the catheter from the heart.

* * * * *